US010023907B2

(12) United States Patent
Van Eijk et al.

(10) Patent No.: US 10,023,907 B2
(45) Date of Patent: Jul. 17, 2018

(54) HIGH THROUGHPUT DETECTION OF MOLECULAR MARKERS BASED ON AFLP AND HIGH THROUGH-PUT SEQUENCING (71) Applicant: Keygene N.V., Wageningen (NL)

(72) Inventors: Michael Josephus Theresia Van Eijk, Herpen (NL); Rene Cornelis Josephus Hogers, Ede (NL)

(73) Assignee: Keygene N.V., Wageningen (NL)

( * ) Notice: Subject to any disclaimer, the term of this patent is extended or adjusted under 35 U.S.C. 154(b) by 776 days.

(21) Appl. No.: 14/285,430

(22) Filed: May 22, 2014

(65) Prior Publication Data
US 2014/0303007 A1 Oct. 9, 2014

Related U.S. Application Data (63) Continuation of application No. 13/449,629, filed on Apr. 18, 2012, now abandoned, which is a continuation of application No. 13/364,799, filed on Feb. 2, 2012, now abandoned, which is a continuation of application No. 12/296,009, filed as application No. PCT/NL2007/000094 on Apr. 4, 2007, now abandoned.

(60) Provisional application No. 60/788,706, filed on Apr. 4, 2006, provisional application No. 60/880,052, filed on Jan. 12, 2007.

(51) Int. Cl.
C12P 19/34 (2006.01)
C12Q 1/6855 (2018.01)
C12Q 1/6853 (2018.01)

(52) U.S. Cl.
CPC ......... C12Q 1/6855 (2013.01); C12Q 1/6853 (2013.01)

(58) Field of Classification Search
CPC ............ C12Q 1/6853; C12Q 2525/155; C12Q 2525/191; C12Q 2535/122; C12Q 2535/138; C12Q 1/6855
USPC ....................................................... 435/91.2
See application file for complete search history.

(56) References Cited

U.S. PATENT DOCUMENTS

| 5,759,822 | A | 6/1998 | Chenchik et al. |
| 5,908,978 | A | 6/1999 | Amerson et al. |
| 5,955,276 | A | 9/1999 | Morgante et al. |
| 6,013,445 | A | 1/2000 | Albrecht et al. |
| 6,045,994 | A | 4/2000 | Zabeau et al. |
| 6,090,556 | A | 7/2000 | Kato |
| 6,100,030 | A | 8/2000 | Feazel et al. |
| 6,232,067 | B1 | 5/2001 | Hunkapiller et al. |
| 6,248,526 | B1 | 6/2001 | Weimer |
| 6,480,791 | B1 | 11/2002 | Strathmann |
| 6,534,293 | B1 | 3/2003 | Barany et al. |
| 6,887,666 | B1 | 5/2005 | Hager |
| 7,217,516 | B2 | 5/2007 | Van Eijk et al. |
| 7,220,549 | B2 | 5/2007 | Buzby |
| 7,300,751 | B2 | 11/2007 | Li et al. |
| 7,323,305 | B2 | 1/2008 | Leamon et al. |
| 7,935,488 | B2 | 5/2011 | Keygene |
| 8,614,073 | B2 | 12/2013 | Van Eijk et al. |
| 9,376,719 | B2 | 6/2016 | Eijk et al. |
| 9,574,230 | B2 | 2/2017 | Van Eijk et al. |
| 2002/0025532 | A1 | 2/2002 | Huang et al. |
| 2002/0106649 | A1 | 8/2002 | Lizardi et al. |
| 2002/0198371 | A1 | 12/2002 | Wang |
| 2003/0165923 | A1 | 9/2003 | Li et al. |
| 2003/0190645 | A1 | 10/2003 | Van Eijk et al. |
| 2003/0207279 | A1 | 11/2003 | Crothers et al. |
| 2004/0029155 | A1 | 2/2004 | Rothberg et al. |
| 2004/0053236 | A1* | 3/2004 | McCallum ............ C12N 15/01 435/6.16 |
| 2004/0081996 | A1 | 4/2004 | Landers et al. |
| 2004/0086912 | A1 | 5/2004 | Luo et al. |
| 2004/0101835 | A1 | 5/2004 | Willis et al. |
| 2004/0157238 | A1 | 8/2004 | Quinn et al. |
| 2004/0185484 | A1 | 9/2004 | Costa et al. |
| 2004/0203032 | A1 | 10/2004 | Lander et al. |
| 2005/0059065 | A1 | 3/2005 | Brenner |
| 2005/0064406 | A1 | 3/2005 | Zabarovsky et al. |
| 2005/0095645 | A1 | 5/2005 | Jones et al. |
| 2005/0130173 | A1* | 6/2005 | Leamon ............ B01L 3/502707 506/2 |

(Continued)

FOREIGN PATENT DOCUMENTS

EP 0 534 858 A1 3/1993
EP 0 976 835 2/2000

(Continued)

OTHER PUBLICATIONS

Nathalie J. van Orsouw et al., PLoS One, Issue 11, e1172, pp. 1-10, Nov. 2007.*
Bensch, et al. "Ten years of AFLP in ecology and evolution: why so few animals?", Molecular Ecology, Sep. 2005, vol. 14, Issue 10, pp. 2899-2914.
Breyne, et al. "Transcriptome analysis during cell division in plants", PNAS, Nov. 12, 2002, vol. 99, No. 23, pp. 14825-14830.
Communication (EP Search Report) in EP Appln No. 10186841.2 dated Aug. 5, 2011.
Data sheet DraI, download from the internet, http://www.neb.com/nebecomm/products, printed on Dec. 18, 2010, p. 1.
Fujiki, et al. "Genetic evidence for CFTR dysfunction in Japanese: background for chronic pancreatitis", J Med Genet, 2004, vol. 41, 6 pgs.

(Continued)

Primary Examiner — Cynthia B Wilder
(74) Attorney, Agent, or Firm — Sunit Talapatra; Foley & Lardner LLP (57) ABSTRACT The present invention relates to a high throughput method for the identification and detection of molecular markers wherein restriction fragments are generated and suitable adaptors comprising (sample-specific) identifiers are ligated. The adapter-ligated restriction fragments may be selectively amplified with adaptor compatible primers carrying selective nucleotides at their 3' end. The amplified adapter-ligated restriction fragments are, at least partly, sequenced using high throughput sequencing methods and the sequence parts of the restriction fragments together with the sample-specific identifiers serve as molecular marker.

12 Claims, 2 Drawing Sheets

(56) References Cited

U.S. PATENT DOCUMENTS

| | | |
|---|---|---|
| 2005/0153317 A1 | 7/2005 | Denise et al. |
| 2005/0181408 A1 | 8/2005 | Brenner |
| 2005/0233354 A1 | 10/2005 | Kennedy |
| 2006/0177832 A1 | 8/2006 | Brenner |
| 2006/0177833 A1 | 8/2006 | Brenner |
| 2007/0020640 A1 | 1/2007 | McCloskey et al. |
| 2007/0172873 A1 | 7/2007 | Brenner et al. |
| 2008/0032287 A1 | 2/2008 | Cantor et al. |
| 2008/0194418 A1 | 8/2008 | Johnson et al. |
| 2009/0005259 A1 | 1/2009 | Drmanac |
| 2009/0142758 A1 | 6/2009 | Van Eijk et al. |
| 2009/0208943 A1 | 8/2009 | Van Eijk et al. |
| 2017/0137872 A1 | 5/2017 | Van Eijk et al. |
| 2017/0166962 A1 | 6/2017 | Van Eijk et al. |
| 2017/0206314 A1 | 7/2017 | Van Eijk et al. |

FOREIGN PATENT DOCUMENTS

| | | |
|---|---|---|
| EP | 1 124 990 | 8/2001 |
| EP | 1 362 929 A2 | 11/2003 |
| EP | 1 574 585 | 9/2005 |
| EP | 1 634 956 B1 | 3/2006 |
| JP | 2000-041687 | 2/2000 |
| JP | 2002-537855 | 11/2002 |
| JP | 2004-113241 | 4/2004 |
| JP | 2004-208586 | 7/2004 |
| JP | 2005-021149 | 1/2005 |
| WO | WO-90/08821 | 8/1990 |
| WO | WO 93/06239 | 4/1993 |
| WO | WO-96/04393 | 2/1996 |
| WO | WO-98/51789 | 11/1998 |
| WO | WO-00/24937 A2 | 5/2000 |
| WO | WO-00/24939 | 5/2000 |
| WO | WO-00/53802 | 9/2000 |
| WO | WO-00/61800 A2 | 10/2000 |
| WO | WO-00/61801 | 10/2000 |
| WO | WO-00/78945 | 12/2000 |
| WO | WO-01/21840 | 3/2001 |
| WO | WO-01/38572 | 5/2001 |
| WO | WO-01/75167 A1 | 10/2001 |
| WO | WO-01/88189 | 11/2001 |
| WO | WO-03/012118 | 2/2003 |
| WO | WO-2004/022758 | 3/2004 |
| WO | WO-2004/057017 | 7/2004 |
| WO | WO-2004/063323 | 7/2004 |
| WO | WO 2005/003375 A | 1/2005 |
| WO | WO 2005/065814 A | 7/2005 |
| WO | WO 2006/137733 A | 12/2006 |
| WO | WO-2006/137734 | 12/2006 |

OTHER PUBLICATIONS

Griffin, et al. "Single-nucleotide polymorphism analysis by MALDI-TOF mass spectrometry", TIBTECH, Feb. 2000, vol. 18, pp. 77-84.

International Search Report in PCT/NL2006/000648 dated May 14, 2007.

Lewis, et al. "High-Density Detection of Restriction-Site-Associated DNA Markers for Rapid Mapping of Mutated Loci in Neurospora", Genetics, Oct. 2007, vol. 177, pp. 1165-1171.

Lindstedt, et al. "A variation fo the amplified-fragment length polymorphism (AFLP) technique using three restriction endonucleases, and assessment of the enzyme combination BgIII-MfeI for AFLP analysis of Salmonella enterica subsp. enterica isolates", FEMS Microbiology Letters, 2000, vol. 189, pp. 19-24.

Lizardi, et al. "Mutation detection and single-molecule counting using isothermal rolling-circle amplification", Nature Genetics, Jul. 1998, vol. 19, pp. 225-232.

Marth, et al. "A general approach to single-nucleotide polymorphism discovery", Nature Genetics, Dec. 1999, vol. 23, pp. 452-456.

Meksem, et al. "Conversion of AFLP bands into high-throughput DNA markers", MGG—Molecular Genetics and Genomics, Apr. 2001, vol. 265, No. 2, pp. 207-214.

Nakai, et al. "Highly Multiplexed Genotyping of Coronary Artery Disease-Associated SNPs Using MALDI-TOF Mass Spectrometry", Human Mutation, 2002, vol. 20, pp. 133-138.

Nicod, et al. "SNPs by AFLP (SBA): a rapid SNP isolation strategy for non-model organisms", Nucleic Acids Research, 2003, vol. 31, No. 5, e19, 5 pgs.

Office Action in JP Appln No. 2008-547127 dated Dec. 5, 2012.

Reijans, et al. "Quantitative comparison of cDNA-AFLP, microarrays, and GeneChip expression data in Saccharomyces cerevisiae", Genomics, 2003, vol. 82, pp. 606-618.

Sallaud, et al. "Highly efficient production and characterization of T-DNA plants for rice (Oryza sativa L.) functional genomics", Theor Appl Genet, 2003, vol. 106, pp. 1396-1408.

Savelkoul, et al. "Amplified-Fragment Length Polymorphism Analysis: the State of an Art", Journal of Clinical Microbiology, 1999, vol. 37, No. 10, pp. 3083-3091.

Shendure, et al. "Accurate Multiplex Polony Sequencing of an Evolved Bacterial Genome", Science, Sep. 9, 2005, vol. 309, pp. 1728-1732.

Simko, I. "One potato, two potato: haplotype association mapping in autotetraploids", Trends in Plant Science, vol. 9, No. 9, Sep. 2004, pp. 441-448.

Truong et al, "Sequence-Based Genotyping for Marker Discovery and Co-Dominant Scoring in Germplasm and Populations," May 2012, PLoS One, vol. 7, No. 5, e37565, pp. 1-9.

Van Der Meulen, et al. "Highly automated AFLP fingerprint analysis on the MegaBACE capillary sequencer", Plant, Animal & Microbe Genomes X Conference, Jan. 12-16, 2002, p. 228, pp. 135.

454 Life Science, "Keygene Selects 454 Life Sciences' Novel Sequencing Technology to Enable Large-Scale SNP Discovery and Detection in Higher Eukaryotic Organisms," News & Events—Press Releases, 2006, pp. 1-2, [XP002452166], Internet: URl:http://www.454.com/news-events/press-releases.asp?display=detail&id=46.

Altshuler, et al. "An SNP map of the human genome generated by reduced representation shotgun sequencing", Nature, vol. 207, Sep. 2000, pp. 513-516.

Amos, CI. et al., "DNA Pooling in Mutation Detection with Reference to Sequence Analysis", American Journal of Human Genetics, vol. 66, 2000, pp. 1689-1692.

Antoine, Janssen, et al., "Application of Corps? Technology for SNP Marker Discovery in Maize," Plant & Animal Genomes XV Conference, 2007, p. 1 [XP002452171], Internet: URL:http://www.intl-pag.org/15/abstracts/PAG15_PO3e_183.html.

Baird, et al., "Rapid SNP Discovery and Genetic Mapping Using Sequenced RAD Markers", PLoS ONE, Oct. 2008, vol. 3, issue 10, e3376, pp. 1-7.

Church, et al., "Multipley DNA Sequencing", Research Articles, Science, vol. 240, Apr. 1988, pp. 185-188.

Colbert, T. et al., "High-Throughput Screening for Induced Point Mutations", Plant Physiology, vol. 126, 2001, pp. 480-484.

Fakhrai-Rad, H. et al., "Prosequencing: An Accurate Detectoin Platform for Single Nucleotide Polymorphisms", Human Mutation, vol. 19, pp. 479-485 (2002).

Gupta, et al. "Single nucleotide polymorphisms: A new paradigm for molecular marker technology and DNA polymorphism detection with emphasis on their use in plants." Current Science, Feb. 2001, vol. 80, No. 4, pp. 524-535.

Lavebratt, C. et al., "Pyrosequencing-Based SNP Allele Frequency Estimation in DNA Pools", Human Mutation, vol. 23, pp. 92-97 (2004).

Lewis, et al., "High-Density Detection of Restriction-Site-Associated DNA Markers for Rapid Mapping of Mutated Loci in Neurospora", Genetics, Oct. 2007, vol. 177, pp. 1163-1171.

Margulies, Marcel, et al., "Genome sequencing in microfabricated high-density picolitre reactors," Nature, 2005, pp. 376-380, vol. 437, No. 7057, Nature Publishing Group, London, GB, [XP002398505].

Miller, et al., "RAD marker microarrays enable rapid mapping of zebrafish mutations", Genome Biology, 2007, vol. 8, Issue 6, Article R105.

(56) References Cited

OTHER PUBLICATIONS

Miller, et al., "Rapid and cost-effective polymorphism identification and genotyping using restriction site associated DNA (RAD) markers", Genome Research, 2007, vol. 17, pp. 240-248.
Nelson, Karen E. et al., "Complete Genome Sequence of the Oral Pathogenic Bacterium Porphyromonas gingivalis Strain W83," Journal of Bacteriology, 2003, vol. 185, No. 18, pp. 5591-5601.
Qiu, F. et al., "DNA Sequence-Based 'Bar Codes' for Tracking the Origins of Expressed Sequence Tags from a Maize eDNA Library Constructed Using Multiple mRNA Sources", Plant Physiology, 133:475-481, Oct. 2003.
Solexa, "Application Note: DNA sequencing," 2006, pp. 1-2, [XP002452169], Internet: URL:http://www.fasteris.com/pdf/DNASeq_AppNote_10_5_06.pdf.
Sood, et al., Method for reverse genetic screening in zebrafish by resequencing and TILLING, Methods, vol. 29, 2006, pp. 220-227.
Stemple, D.L., "TILLING—a high-throughput harvest for functional genomics", Nature Reviews, vol. 5, pp. 1-6 (2004).
Till, et al. "Large-scale discovery of induced point mutations with high-throughput TILLING." Genome Research, Mar. 2003, vol. 13, No. 3, pp. 524-530.
Van Eijk, et al., "Complexity Reduction of Polymorphic Sequences (CRoPS): A Novel Approach for High Throughput Polymorphism Discovery," Plant and Animal Genomes XIV Conference, 2006, p. 1, [XP002452165], Internet: URL:http://www.intl-pag.org/14/abstracts/PAG14_W410.html.
Van Eijk, et al., "Sequence-Based AFLP® Detection Using Solexa's Clonal Single Molecule Array (CSMA?) Technology," Plant & Animal Genomes XV Conference, 2007, p. 1, [XP002452170], Internet: URL:http://www.intl-pag.org/15/abstracts/PAG15_P02c_69.html.
Vandenbussche, et al. "Toward the analysis of the petunia MADS box gene family by reverse and forward transposon insertion mutagenesis approaches: B, C, and D floral organ identify functions require SEPALLATA-like MADS box genes in petunia." The Plant Cell, Nov. 2003, vol. 15, No. 11, pp. 2680-2693.
Vieux, E. F. et al., "Primer Design for PCR and Sequencing in High-Throughput Analysis of SNPs", BioTechniques, vol. 32, pp. S28-S32 (2002).
Vos, P., et al., "AFLP: A New Technique for DNA fingerprinting," Nucleic Acids Research, 1995, pp. 4407-4414, vol. 23, No. 21, Oxford University Press, Surrey, GB, [XP000939214].
Wineholds, et al. "Efficient Target-selected mutagenesis in zebrafish." Genome Research, Dec. 2003, vol. 13, No. 12, pp. 2700-2707.
Wineholds, et al. "Target-selected gene inactivation in zebrafish.", Methods in Cell Biology, 2004, vol. 77, pp. 69-90.
World's Technology News, "Solexa to Conduct Technology Seminar at the American Society of Human Genetics Conference", 2005, p. 1, [XP002452168], Internet: URL:http://www.mirror99.com/20051028/solexa_to_conduct_technology_seminar_at_the_american_society_of_human_genetics_bhfd.jspx.
U.S. Appl. No. 90/013,467.
Mueller, et al. "AFLP genotyping and fingerprinting", Tree (Oct. 1999), vol. 14, No. 10, pp. 389-394.
U.S. Appl. No. 15/674,126, filed Aug. 10, 2017, Van Eijk et al.
U.S. Appl. No. 15/683,252, filed Aug. 22, 2017, Van Eijk et al.
U.S. Appl. No. 15/707,650, filed Sep. 18, 2017, Van Eijk et al.
U.S. Appl. No. 15/729,328, filed Oct. 10, 2017, Van Eijk et al.
"Instruction Manual AFLP Analysis System 1-7 II AFLP Small Genome Primer Kit", Jan. 22, 2003, retrieved from URL: https://nature.berkeley.edu/brunslab/ftp/aflpii.pdf.
Bishop, et al. "Analysis of the transcriptome of the protozoan Theileria parva using MPSS reveals that the majority of genes are transcriptionally active in the schizont stage", Nucleic Acids Research, 2005, vol. 33, No. 17, pp. 5503-5511.
Bouzidi, et al., "A sunflower BAC library suitable for PCR screening and physical mapping of targeted genomic regions.", TAG, vol. 113, No. 1, 2006, pp. 81-89.

Brenner, et al., "DNA fingerprinting by sampled sequencing", Proc. Natl. Acad. Sci., Nov. 1989, vol. 86, pp. 8902-8906.
Dong, et al. "Flexible Use of High-Density Oligonucleotide Arrays for Single-Nucelotide Polymorphism Discovery and Validation", Genome Research, 2001, vol. 11, No. 8, pp. 1418-1424.
Duprat et al., "The Arabidopsis eukaryotic initiation factor (iso) 4E is dispensable for plant growth but required for susceptibility to potyviruses", The Plant Journal, 2002, vol. 32, pp. 927-934.
Epinat et al., "A novel engineered meganuclease induces homologous recombination in yeast and mammalian cells", Nucleic Acids Research, 2003, vol. 31, No. 11, pp. 2952-2962.
Greene et al., "Spectrum of chemically induced mutations from a large-scale reverse-genetic screen in Arabidopsis", Genetics, Jun. 2003, vol. 164, pp. 731-740.
Gregory, et al., "Genome Mapping by Fluorescent Fingerprinting", Genome Research, 1997, vol. 7, pp. 1162-1168.
Gruber, et al. "Estimation of single nucleotide polymorphism allele frequency in DNA pools by using Pyrosequencing", Hum Genet (2002), vol. 110, pp. 395-401.
Havre et al., "Targested mutagenesis of DNA using triple helix-forming oligonucleotides linked to psoralen", Proc. Natl. Acad. Sci, Aug. 1993, vol. 90, pp. 7879-7883.
Henikoff, et al. "TILLING. Traditional Mutagenesis Meets Functional Genomics", Plant Physiology, Jun. 2004, vol. 135, pp. 630-636.
Hug et al., "Measurement of the number of molecules of a single mRNA species in a complex mRNA preparation", J. theor. Biol., 2003, vol. 221, pp. 615-624.
Iwahana, et al. "T-cassette Ligation: A Method for Direct Sequencing and Cloning of PCR-amplified DNA Fragments", PCR Methods and Applications, 1994, pp. 219-224.
Jamsari, et al., "BAC-derived diagnostic markers for sex determination in asparagus.", Theoretical and Applied Genetics, vol. 108, No. 6, 2004, pp. 1140-1146.
Jordan, et al. "Genome complexity reduction for SNP genotyping analysis", PNAS, Mar. 5, 2002, vol. 99, No. 5, pp. 2942-2947.
Klein, et al., "A high-throughput AFLP-based method for constructing integrated genetic and physical maps: Progress toward a sorghum genome map", Genome Research, vol. 10, No. 5, 2000, pp. 789-807.
Lehninger, "The Principles of Biochemistry", The Johns Hopkins University School of Medicine, Nov. 1982, Table of Contents.
Li et al., "A fast neutron deletion mutagenesis-based reverse genetics system for plants", The Plant Journal, 2001, vol. 27, No. 3, pp. 235-242.
Lloyd et al., "Targeted mutagenesis using zinc-finger nucleases in Arabidopsis", PNAS, Feb. 8, 2005, vol. 102, No. 6, pp. 2232-2237.
Marra, et al., "High Throughput Fingerprint Analysis of Large-Insert Clones", Genome Research, 1997, vol. 7, pp. 1072-1084.
Matsuzaki, et al. "Parallel Genotyping of Over 10,000 SNPs Using a One-Primer Assay on a High-Density Oligonucleotide Array" Genome Research (Mar. 2004) vol. 14, No. 3, pp. 414-425.
McCallum et al., "Targeting Induced LocalLesions INGenomes (TILLING) for Plant Functional Genomics", Plant Physiology (2000), vol. 123, No. 2, pp. 439-442.
McCallum, et al., "Targeted Screening for Induced Mutations", Nature Biotechnology (Apr. 2000), vol. 18, No. 4, pp. 455-457.
Meissner et al., "Reduced representation bisulfite sequencing for comparative high-resolution DNA methylation analysis", Nucleic Acids Research, 2005, vol. 3, No. 18, pp. 5868-5877.
Menda et al., "In silico screening of a saturated mutation library of tomato", The Plant Journal, 2004, vol. 38, pp. 861-872.
Meyers, et al. "Analysis of the transcriptional complexity of Arabidopsis thaliana by massively parallel signature sequencing", Nature Biotechnology, Aug. 2004, vol. 22, No. 8, pp. 1006-1011.
Miller et al., "A comprehensive approach to clustering of expressed human gene sequence: the sequence tag alignment and consensus knowledge base", Genome Research, 1999, vol. 9, pp. 1143-1155.
Nair, et al. "PCR-based DNA markers linked to a gall midge resistance gene, Gm4t, has potential for marker-aided selection in rice", Theor Appl Genet (1996), vol. 92, pp. 660-665.

(56) References Cited

OTHER PUBLICATIONS

Nicaise et al., "The eukaryotic translation initiation factor 4E controls lettuce susceptibility to the potyvirus Lettuce mosaic virus1", Plant Physiology, Jul. 2003, vol. 132, pp. 1272-1282.

Rafalski "Applications of single nucleotide polymorphisms in crop genetics", Current Opinion in Plant Biology (2002) vol. 5, pp. 94-100.

Retrieved from EBI accession No. UNIPROT:C5Z1DO, Sep. 1, 2009, "RecName: Full=Pectinesterase; EC=3.1.1.11;".

Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor;".

Ruffel et al., "A natural recessive resistance gene against potato virus Y in pepper corresponds to the eukaryotic initiation factor 4E (eIF4E)", The Plant Journal, 2002, vol. 32, pp. 1067-1075.

Ruffel et al., "The recessive potyvirus resistance gene pot-1 is the tomato orthologue of the pepper pvr2-eIF4E gene" Mol.Gen.Genetics, 2005, vol. 274, pp. 346-353.

Stewart et al., "A rapid CTAB DNA isolation technique useful for RAPD fingerprinting and other PCR applications" Biotechniques, 1993, vol. 14, No. 5., pp. 748-750.

Swindell, "The Association Among Gene Expression Responses to Nine Abiotic Stress Treatments in *Arabidopsis thaliana*", Genetics, Dec. 2006, vol. 1811-1824.

Volkmuth, et al. "Technical Advances: Genome-Wide cDNA-AFLP Analysis of the *Arabidopsis* Transcriptome", A Journal of Integrative Biology, 2003, vol. 7, No. 2, pp. 143-160.

Wienholds, et al. "Target-Selected Inactivation of the Zebrafish rag1 Gene", Science (2002), vol. 297, pp. 99-102.

Wolford, et al., "High-throughput SNP detection by using DNA pooling and denaturing high performance liquid chromatography (DHPLC)", Human Genetics (2000) vol. 107, pp. 83-487.

Xia, et al., "Construction and characterization of a BAC library of soybean.", vol. 141, No. 1-2, 2005, pp. 129-137.

Yuanxin, et al. "T-linker-specific ligation PCR (T-linker PCR): an advanced PCR technique for chromosome walking or for isolation of tagged DNA ends", Nucleic Acids Research, 2003, vol. 31, No. 12, e68, 7 pgs.

Miner "Molecular barcodes detect redundancy and contamination in hairpin-bisulfite PCR", Nucleic Acids Research, 2004, vol. 32, No. 17, 4 pages.

* cited by examiner

Ligate IIs adaptors

Adaptor structure:

Primer structure:

SEQUENCE LISTING

```
<160> NUMBER OF SEQ ID NOS: 7

<210> SEQ ID NO 1
<211> LENGTH: 14
<212> TYPE: DNA
<213> ORGANISM: Zea mays

<400> SEQUENCE: 1
cggcgacgta ccgc                                                        14

<210> SEQ ID NO 2
<211> LENGTH: 14
<212> TYPE: DNA
<213> ORGANISM: Zea mays

<400> SEQUENCE: 2
ctagtaatta ttcc                                                        14

<210> SEQ ID NO 3
<211> LENGTH: 14
<212> TYPE: DNA
<213> ORGANISM: Zea mays

<400> SEQUENCE: 3
cagcgccttc tcct                                                        14

<210> SEQ ID NO 4
<211> LENGTH: 14
<212> TYPE: DNA
<213> ORGANISM: Zea mays

<400> SEQUENCE: 4
cagaactctg actt                                                        14

<210> SEQ ID NO 5
<211> LENGTH: 14
<212> TYPE: DNA
<213> ORGANISM: Zea mays

<400> SEQUENCE: 5
caaatctgtt agat                                                        14

<210> SEQ ID NO 6
<211> LENGTH: 14
<212> TYPE: DNA
<213> ORGANISM: Zea mays

<400> SEQUENCE: 6
catgaaggat ttat                                                        14

<210> SEQ ID NO 7
<211> LENGTH: 14
<212> TYPE: DNA
<213> ORGANISM: Zea mays

<400> SEQUENCE: 7
caaacagaca accg                                                        14
```

HIGH THROUGHPUT DETECTION OF MOLECULAR MARKERS BASED ON AFLP AND HIGH THROUGH-PUT SEQUENCING

This application is a continuation of U.S. application Ser. No. 13/449,629, filed Apr. 18, 2012, which is a continuation of U.S. application Ser. No. 13/364,799, filed Feb. 2, 2012; which is a continuation of U.S. application Ser. No. 12/296,009, filed Feb. 6, 2009, now abandoned; which is the U.S. national stage of International Application No. PCT/NL2007/000094, filed Apr. 4, 2007; which claims priority to U.S. Provisional Application Nos. 60/788,706, filed Apr. 4, 2006; and 60/880,052, filed Jan. 12, 2007. Each application is incorporated herein in its entirety.

FIELD OF THE INVENTION

The present invention relates to the field of molecular biology and biotechnology. In particular, the invention relates to the field of nucleic acid detection identification. More in particular the invention relates to methods for the detection and identification of markers, in particular molecular markers. The invention is concerned with the provision of high throughput methods for the detection and identification of molecular markers. The invention further relates to the application of the method in the identification of and/or detection of nucleotide sequences that are related to a wide variety of genetic traits, genes, haplotypes and combinations thereof. The invention can be used in the field of high throughput detection and identification of molecular markers from any origin, be it plant, animal, human, artificial or otherwise.

BACKGROUND OF THE INVENTION

Exploration of genomic DNA has long been desired by the scientific, in particular medical, community. Genomic DNA holds the key to identification, diagnosis and treatment of diseases such as cancer and Alzheimer's disease. In addition to disease identification and treatment, exploration of genomic DNA may provide significant advantages in plant and animal breeding efforts, which may provide answers to food and nutrition problems in the world.

Many diseases are known to be associated with specific genetic components, in particular with polymorphisms in specific genes. The identification of polymorphisms in large samples such as genomes is at present a laborious and time-consuming task. However, such identification is of great value to areas such as biomedical research, developing pharmacy products, tissue typing, genotyping and population studies.

Markers, i.e. genetic markers, have been used for a very long time as a genetic typing method, i.e. to connect a phenotypic trait to the presence, absence or amount of a particular part of DNA (gene). One of the most versatile genetic typing technologies is AFLP, already around for many years and widely applicable to any organism (for reviews see Savelkoul et al. J. Clin. Microbiol, 1999, 37(10), 3083-3091; Bensch et al. Molecular Ecology, 2005, 14, 2899-2914)

The AFLP technology (Zabeau & Vos, 1993; Vos et al., 1995) has found widespread use in plant breeding and other field since its invention in the early nineties. This is due to several characteristics of AFLP, of which the most important is that no prior sequence information is needed to generate large numbers of genetic markers in a reproducible fashion. In addition, the principle of selective amplification, a cornerstone of AFLP, ensures that the number of amplified fragments can be brought in line with the resolution of the detection system, irrespective of genome size or origin.

Detection of AFLP fragments is commonly carried out by electrophoresis on slab-gels (Vos et al., 1995) or capillary electrophoresis (van der Meulen et al., 2002). The majority of AFLP markers scored in this way represent (single nucleotide) polymorphisms occurring either in the restriction enzyme recognition sites used for AFLP template preparation or their flanking nucleotides covered by selective AFLP primers. The remainder of the AFLP markers are insertion/deletion polymorphisms occurring in the internal sequences of the restriction fragments and a very small fraction on single nucleotide substitutions occurring in small restriction fragments (<approximately 100 bp), which for these fragments cause reproducible mobility variations between both alleles which can be observed upon electrophoresis; these AFLP markers can be scored co-dominantly without having to rely on band intensities.

In a typical AFLP fingerprint, the AFLP markers therefore constitute the minority of amplified fragments (less than 50 percent but often less than 20 percent), while the remainder are commonly referred to as constant AFLP fragments. The latter are nevertheless useful in the gel scoring procedure as they serve as anchor points to calculate fragments mobilities of AFLP markers and aid in quantifying the markers for co-dominant scoring. Co-dominant scoring (scoring for homo- or heterozygosity) of AFLP markers currently is restricted to the context of fingerprinting a segregating population. In a panel of unrelated lines, only dominant scoring is possible.

Although the throughput of AFLP is very high due to high multiplexing levels in the amplification and detection steps, the rate limiting step is the resolving power of electrophoresis. Electrophoresis allows unique identification of the majority of amplified fragments based on the combination of restriction enzyme combinations (EC), primer combinations (PC) and mobility, but electrophoresis is only capable to distinguish the amplified fragments based on differences in mobility. Fragments of similar mobility are often found as so-called 'stacked bands' and with electrophoresis, no attention can be given to the information that is contained in so-called 'constant bands', i.e. amplified restriction fragments that do not appear to differ between compared species. Furthermore on a typical gel-based system, or on a capillary system such as a MegaBACE, samples must be run in parallel and only about 100-150 bands per lane on a gel or per capillary can be analysed. These limitations also hamper throughput.

Ideally, the detection system should be capable of determining the entire sequence of the amplified fragments to capture all amplified restriction fragments. However, most high throughput sequencing technologies cannot yet provide sequencing reads that encompass entire AFLP fragments, which are typically 100-500 bp in length.

So far, detection of AFLP markers/sequences by sequencing has not been economically feasible due to, among other limitations, cost limitations of Sanger dideoxy sequencing technology and other conventional sequencing technologies.

Detection by sequencing instead of mobility determination will increase throughput because:

1) polymorphisms located in the internal sequences will be detected in most (or all) amplified fragments; this will increase the number of markers per PC considerably.

2) no loss of AFLP markers due to co-migration of AFLP markers and constant bands.

3) co-dominant scoring does not rely on quantification of band intensities and is independent of the relatedness of the individuals fingerprinted.

However, detection by sequencing of the entire restriction fragment is still relatively uneconomical. Furthermore, the current state of the art sequencing technology such as disclosed herein elsewhere (from 454 Life Sciences, www.454.com and Solexa, www.solexa.com), despite their overwhelming sequencing power, can only provide sequencing fragments of limited length. Also the current methods do not allow for the simultaneous processing of many samples in one run.

Definitions

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Nucleic acid: a nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

AFLP: AFLP refers to a method for selective amplification of nucleic acids based on digesting a nucleic acid with one or more restriction endonucleases to yield restriction fragments, ligating adaptors to the restriction fragments and amplifying the adaptor-ligated restriction fragments with at least one primer that is (part) complementary to the adaptor, (part) complementary to the remains of the restriction endonuclease, and that further contains at least one randomly selected nucleotide from amongst A, C, T, or G (or U as the case may be). AFLP does not require any prior sequence information and can be performed on any starting DNA. In general, AFLP comprises the steps of:

(a) digesting a nucleic acid, in particular a DNA or cDNA, with one or more specific restriction endonucleases, to fragment the DNA into a corresponding series of restriction fragments;

(b) ligating the restriction fragments thus obtained with a double-stranded synthetic oligonucleotide adaptor, one end of which is compatible with one or both of the ends of the restriction fragments, to thereby produce adaptor-ligated, preferably tagged, restriction fragments of the starting DNA;

(c) contacting the adaptor-ligated, preferably tagged, restriction fragments under hybridizing conditions with one or more oligonucleotide primers that contain selective nucleotides at their 3'-end;

(d) amplifying the adaptor-ligated, preferably tagged, restriction fragment hybridised with the primers by PCR or a similar technique so as to cause further elongation of the hybridised primers along the restriction fragments of the starting DNA to which the primers hybridised; and (e) detecting, identifying or recovering the amplified or elongated DNA fragment thus obtained.

AFLP thus provides a reproducible subset of adaptor-ligated fragments. AFLP is described in EP 534858, U.S. Pat. No. 6,045,994 and in Vos et al. Reference is made to these publications for further details regarding AFLP. The AFLP is commonly used as a complexity reduction technique and a DNA fingerprinting technology. Within the context of the use of AFLP as a fingerprinting technology, the concept of an AFLP marker has been developed.

AFLP marker: An AFLP marker is an amplified adaptor-ligated restriction fragment that is different between two samples that have been amplified using AFLP (finger-printed), using the same set of primers. As such, the presence or absence of this amplified adaptor-ligated restriction fragment can be used as a marker that is linked to a trait or phenotype. In conventional gel technology, an AFLP marker shows up as a band in the gel located at a certain mobility. Other electrophoretic techniques such as capillary electrophoresis may not refer to this as a band, but the concept remains the same, i.e. a nucleic acid with a certain length and mobility. Absence or presence of the band may be indicative of (or associated with) the presence or absence of the phenotype. AFLP markers typically involve SNPs in the restriction site of the endonuclease or the selective nucleotides. Occasionally, AFLP markers may involve indels in the restriction fragment.

Constant band: a constant band in the AFLP technology is an amplified adaptor-ligated restriction fragment that is relatively invariable between samples. Thus, a constant band in the AFLP technology will, over a range of samples, show up at about the same position in the gel, i.e. has the same length/mobility. In conventional AFLP these are typically used to anchor the lanes corresponding to samples on a gel or electropherograms of multiple AFLP samples detected by capillary electrophoresis. Typically, a constant band is less informative than an AFLP marker. Nevertheless, as AFLP markers customary involve SNPs in the selective nucleotides or the restriction site, constant bands may comprise SNPs in the restriction fragments themselves, rendering the constant bands an interesting alternative source of genetic information that is complementary to AFLP markers.

Selective base: Located at the 3' end of the primer that contains a part that is complementary to the adaptor and a part that is complementary to the remains of the restriction site, the selective base is randomly selected from amongst A, C, T or G. By extending a primer with a selective base, the subsequent amplification will yield only a reproducible subset of the adaptor-ligated restriction fragments, i.e. only the fragments that can be amplified using the primer carrying the selective base. Selective nucleotides can be added to the 3'end of the primer in a number varying between 1 and 10. Typically 1-4 suffice. Both primers may contain a varying number of selective bases. With each added selective base, the subset reduces the amount of amplified adaptor-ligated restriction fragments in the subset by a factor of about 4. Typically, the number of selective bases used in AFLP is indicated by +N+M, wherein one primer carries N selective nucleotides and the other primers carries M selective nucleotides. Thus, an Eco/Mse+1/+2 AFLP is shorthand for the digestion of the starting DNA with EcoRI and MseI, ligation of appropriate adaptors and amplification with one primer directed to the EcoRI restricted position carrying one selective base and the other primer directed to the MseI restricted site carrying 2 selective nucleotides. A primer used in AFLP that carries at least one selective nucleotide at its 3' end is also depicted as an AFLP-primer. Primers that do not carry a selective nucleotide at their 3' end and which in fact are complementary to the adaptor and the remains of the restriction site are sometimes indicated as AFLP+0 primers.

Clustering: with the term "clustering" is meant the comparison of two or more nucleotide sequences based on the presence of short or long stretches of identical or similar nucleotides. Several methods for alignment of nucleotide sequences are known in the art, as will be further explained below. Sometimes the terms "assembly" or "alignment" are used as synonyms.

Identifier: a short sequence that can be added to an adaptor or a primer or included in its sequence or otherwise used as label to provide a unique identifier. Such a sequence identifier can be a unique base sequence of varying but defined length uniquely used for identifying a specific nucleic acid sample. For instance 4 bp tags allow 4(exp4)=256 different tags. Typical examples are ZIP sequences, known in the art as commonly used tags for unique detection by hybridization (Iannone et al. Cytometry 39:131-140, 2000). Using such an identifier, the origin of a PCR sample can be determined upon further processing. In the case of combining processed products originating from different nucleic acid samples, the different nucleic acid samples are generally identified using different identifiers.

Sequencing: The term sequencing refers to determining the order of nucleotides (base sequences) in a nucleic acid sample, e.g. DNA or RNA.

High-throughput screening: High-throughput screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

Restriction endonuclease: a restriction endonuclease or restriction enzyme is an enzyme that recognizes a specific nucleotide sequence (target site) in a double-stranded DNA molecule, and will cleave both strands of the DNA molecule at or near every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Gel electrophoresis: in order to detect restriction fragments, an analytical method for fractionating DNA molecules on the basis of size can be required. The most commonly used technique for achieving such fractionation is (capillary) gel electrophoresis. The rate at which DNA fragments move in such gels depends on their molecular weight; thus, the distances traveled decrease as the fragment lengths increase. The DNA fragments fractionated by gel electrophoresis can be visualized directly by a staining procedure e.g. silver staining or staining using ethidium bromide, if the number of fragments included in the pattern is sufficiently small. Alternatively further treatment of the DNA fragments may incorporate detectable labels in the fragments, such as fluorophores or radioactive labels, which are preferably used to label one strand of the AFLP product.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g. about 10 to about 30 base pairs in length, which are designed such that they can be ligated to the ends of restriction fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this need not be the case (double ligated adaptors).

Adaptor-ligated restriction fragments: restriction fragments that have been capped by adaptors.

Primers: in general, the term primers refer to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

DNA amplification: the term DNA amplification will be typically used to denote the in vitro synthesis of double-stranded DNA molecules using PCR. It is noted that other amplification methods exist and they may be used in the present invention without departing from the gist.

SUMMARY OF THE INVENTION

The present inventors have found that the above described problems and other problems in the art can be overcome by devising a generic way wherein the versatility and applicability of (AFLP) marker technology can be combined with that of state-of-the-art high throughput sequencing technology.

Thus, the present inventors have found that by incorporation of a sample-specific identifier in the adaptor-ligated restriction fragment and/or the determination of only part of the sequence of the restriction fragment provides for a very efficient and reliable improvement of the existing technologies. It was found that by incorporation of a sample-specific identifier, multiple samples can be sequenced in a single run and by sequencing only part of the restriction fragment, adequate identification of the restriction fragment can be achieved.

BRIEF DESCRIPTION OF THE DRAWINGS

FIG. 1: is a schematic representation of the adaptor structure that is used in a regular AFLP-based approach for AFLP detection short tag sequencing. A typical AFLP fragment derived form a digest of a DNA sample with EcoRI and MseI and subsequent adapter ligation is shown, followed by a typical adaptor for the EcoRI site. The adaptor comprises, from the 5' to 3' end, a 5' primer sequence, which is optional, and can be used to anchor amplification primers or to anchor the adapter-ligated fragment to a bead or surface. Further an identifier is shown (given as NNNNNN in a degenerate form), followed by remains of a recognition sequence of a restriction enzyme (in this EcoRI, i.e. AATTC). The last nucleotide of the identifier preferably does not comprise a G in order to destroy the EcoRI restriction site. A suitable primer is provided that comprises the optional 5' primer sequence, an example of a specific primer (ACTGAC), remains of the recognition site and a section that may contain one or more selective nucleotides at the 3' end.

DETAILED DESCRIPTION OF THE INVENTION

In one aspect, the invention relates to a method for the identification of restriction fragments in a sample, comprising the steps of:
(a) providing a sample nucleic acid;
(b) digesting the sample nucleic acid with at least one restriction endonuclease to obtain a set of restriction fragments;
(c) providing double stranded synthetic adaptors comprising
   a 5' primer-compatible sequence,
   a sample-specific identifier section,
   a section that is complementary to the remains of the recognition sequence of the restriction endonuclease;
(d) ligating the double stranded synthetic adaptors to the restriction fragments in the set, to provide a set of adaptor-ligated restriction fragments;
(e) amplification of the set of adaptor-ligated restriction fragments, with one or more primers that are at least complementary to:
   the sample-specific identifier section,
   the section that is complementary to the remains of the recognition sequence of the restriction endonuclease, to provide for amplified adaptor-ligated restriction fragments (amplicons);
(f) determining the sequence of at least the sample-specific identifier section, the remains of the recognition sequence of the restriction endonuclease and of part of the sequence of the restriction fragment located adjacent thereto of (part of) the amplified adaptor-ligated restriction fragments.
(g) identifying the presence or absence of amplified adaptor-ligated restriction fragments in the sample.

By treating a sample nucleic acid in this way, a set of amplified restriction fragments is obtained for every sample that is sequenced. Every restriction fragment can be identified as originating from a certain sample via the sample specific identifier which is different for each sample. Sequencing of the amplified adaptor-ligated restriction fragments provides sequence information on at least part of the adaptor-ligated restriction fragment. The information contained in the adaptor-derived part contains information about the sample from which the fragment is obtained, whereas sequence information from the restriction fragment itself provides information about the restriction fragment and allows for identification of the restriction fragment. This sequence information on the restriction fragment is used to identify the restriction fragment with an accuracy that depends on the number of nucleotides that is determined and the number of restriction fragments in the set of amplified adaptor-ligated restriction fragments.

To provide a solution to the problem of sampling variation which affects the accuracy of identifying molecular markers by sequencing contained in a set of multiple fragments, the present inventors have also found that detection of markers via sequencing is preferably performed with sufficient redundancy (depth) to sample all amplified fragments at least once and accompanied by statistical means which address the issue of sampling variation in relation to the accuracy of the genotypes called. Furthermore, just as with AFLP scoring, in the context of a segregating population, the simultaneous scoring of the parent individuals in one experiment, will aid in determining the statistical threshold.

Thus, in certain embodiments, the redundancy of the tagged amplified adaptor-ligated restriction fragments is at least 6, preferably at least 7, more preferably at least 8 and most preferably at least 9. In certain embodiments, the sequence of each adaptor-ligated restriction fragment is determined at least 6, preferably at least 7, more preferably at least 8 and most preferably at least 9 fold. In certain embodiments, the redundancy is selected such, assuming a 50/50 overall chance of identifying the locus correctly as homozygous, that the chance of correct identification of the locus is more than 95%, 96%, 97%, 98%, 99%, 99.5%.

In this respect the following calculation may be illustrative: The sequencing technology of Solexa as described herein elsewhere, provides for 40.000.000 reads of about 25 bp each, totaling a staggering 1 billion by in one single run. Assuming a redundancy in sampling of 10 times, 4.000.000 unique fragments can be assessed in one run. Combining 100 samples allows for 40.000 fragments to be sequences for each sample. Seen from the perspective of AFLP, this amounts to 160 primer combinations with 250 fragments each.

This method allows for the identification of restriction fragments in way that is different from that of the conventional marker detection based on electrophoresis.

In the first step of the method for the identification of restriction fragments a sample nucleic acid is provided. The nucleic acids in the sample will usually be in the form of DNA. However, the nucleotide sequence information contained in the sample may be from any source of nucleic acids, including e. g. RNA, polyA+RNA, cDNA, genomic DNA, organellar DNA such as mitochondrial or chloroplast DNA, synthetic nucleic acids, DNA libraries (such as BAC libraries/pooled BAC clones), clone banks or any selection or combinations thereof. The DNA in the nucleic acid sample may be double stranded, single stranded, and double stranded DNA denatured into single stranded DNA. The DNA sample can be from any organism, whether plant, animal, synthetic or human.

The nucleic acid sample is restricted (or digested) with at least one restriction endonuclease to provide for a set of restriction fragments. In certain embodiments, two or more endonucleases can be used to obtain restriction fragments. The endonuclease can be a frequent cutter (a recognition sequence of 3-5 bp, such as MseI) or a rare cutter (recognition sequence of >5 bp, such as EcoRI). In certain preferred embodiments, a combination of a rare and a frequent cutter is preferred. In certain embodiments, in particular when the sample contains or is derived from a relative large genome, it may be preferred to use a third enzyme (rare or frequent cutter) to obtain a larger set of restriction fragments of shorter size.

As restriction endonucleases, any endonuclease will suffice. Typically, Type II endonucleases are preferred such as EcoRI, MseI, PstI etc. In certain embodiments a type IIs endonuclease may be used, i.e. an endonuclease of which the recognition sequence is located distant from the restriction site, i.e such as AceIII, AlwI, AlwXI, Alw26I, BbvI, BbvII, BbsI, BccI, Bce83I, BcefI, BcgI, BinI, BsaI, BsgI, BsmAI, BsmFI, BspMI, EarI, EciI, Eco31I, Eco57I, Esp3I, FauI, FokI, GsuI, HgaI, HinGUII, HphI, Ksp632I, MboII, MmeI, Mn1I, NgoVIII, PleI, RleAI, SapI, SfaNI, TaqJI and ZthII III. The use of this type of restriction endonuclease leads to certain adaptations to the method as will be described herein elsewhere.

Figure 1:
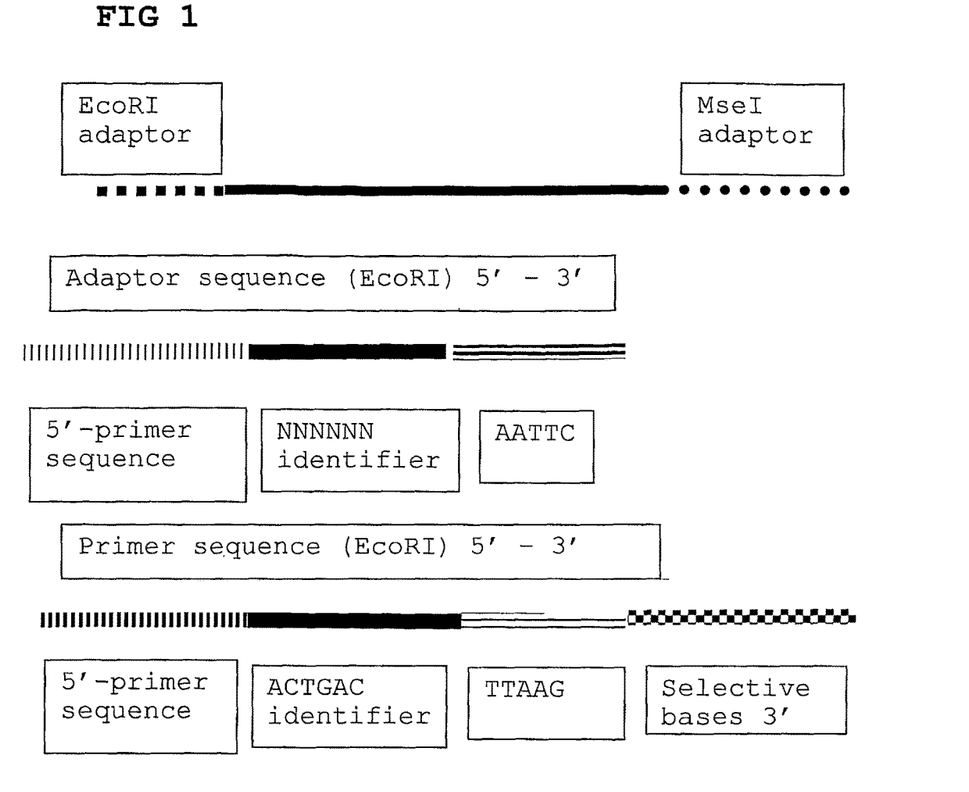

Restriction fragments can be blunt-ended or have protruding ends, depending on the endonuclease used. To these ends, adaptors can be ligated. Typically, the adaptors used in the present invention have a particular design. The adaptors used in the present invention may comprise a 5'-primer compatible sequence, which may be optional to provide for sufficient length of the adaptor for subsequent primer annealing, followed by a sample-specific identifier section that may comprise from 4-16 nucleotides. Preferably the sample-specific identifier does not contain 2 or more consecutive identical bases to prevent readthroughs during the sequencing step. Furthermore, in case 2 or more sample are combined and multiple sample specific identifiers are used to distinguish the origin of the samples, there is preferably a difference between the sample-specific identifiers of at least 2, preferably 3 bp. This allows for improved discrimination between the different sample-specific identifiers within a combined pool of samples. At the 3'end of the adaptor a section is located that is complementary to the remains of the recognition sequence of the restriction endonuclease. For instance, EcoRI recognises 5'-GAATTC-3' and cuts between G and AATTC. For EcoRI, the section complementary to the remains of the recognition sequence of the restriction endonuclease hence is a C-nucleotide.

The adaptor is ligated (covalently connected) with one or both sides of the restriction fragment. When digestion is performed with more than one endonuclease, different adaptors may be used which will give rise to different sets of adaptor-ligated restriction fragments.

The adaptor-ligated restriction fragments are subsequently amplified with a set of one or more primers. The primer may be complementary to the adaptor only, i.e. non-selective amplification. The primer preferably contains a section that is complementary to the sample-specific identifier and a section that is complementary to the remains of the recognition sequence of the restriction endonuclease. In certain embodiments, the primer may contain at its 3'end one or more selective nucleotides to provide for a subset of amplified adapter-ligated restriction fragments. The primer may at its 5'end also contain further nucleotides to aid in anchoring the primer to the adapter-ligated restriction fragments. In certain embodiments, the primer may contain nucleotides that express improved hybridisation characteristics such as LNAs or PNAs. To amplify adapter-ligated restriction fragments from combined samples in a pool it is possible to use sets of degenerated primers, i.e. primer sets wherein for each sample, the corresponding sample-identifier is incorporated in the primer. In certain embodiments, it is possible to use primer sets wherein the identifier section is completely degenerated (or at least to a large extent) i.e. (almost) every combination of nucleotides is provided in the sample specific identifier section. Combined with stringent hybridisation conditions in the amplification and the optional use of LNA or PNA-type nucleotides to increase hybridisation characteristics, this may lead to a very efficient amplification.

The amplification of the adapter-ligated restriction fragments lead to a set of amplified adapter-ligated restriction fragments, sometimes referred to as amplicons.

The amplicons (or at least part thereof) are subjected to a step that comprises at least the determination of the sequence of the sample specific identifier to determine the origin of the fragment and of part of the sequence of the restriction fragment. In practice this amounts also to the determination of the sections located in-between such as the remains of the recognition sequence of the restriction endonuclease. By sequencing the sample specific identifier in combination with part of the fragment located adjacent to the adapter derived sequence, it is possible to uniquely identify restriction fragments. When correlated to the presence or absence of a phenotype, these uniquely identified restriction fragments can be used as molecular markers. This allows for the definition of a new generation of markers and amounts hence to a novel marker technology with the proven versatility of AFLP technology, yet that is suitable for high-throughput technologies and is generally applicable amongst any type of organism or nucleic acid. Uniquely identifying restriction fragments in a sample by determination of part of their sequence by this method can be repeated for multiple samples. The presence or absence of the restriction fragments with the depicted sequence in the sample is indicative for the presence or absence of a phenotype.

A further advantage of the presently invented marker technology based on the combination of AFLP and high throughput sequencing is the additional information that can be obtained compared to conventional AFLP technology. In AFLP, amplicons that are designated as AFLP markers typically contain polymorphism in the recognition site, the restriction site or, optionally, in the selective nucleotides. Polymorphisms located further in the restriction fragment typical do not qualify as AFLP markers (apart from perhaps indel polymorphisms). With the present sequencing step, the nucleotides adjacent to the optional selective nucleotides are also determined and this leads to the identification of an increased number of molecular markers and to an improvement in the existing marker technology.

The high throughput sequencing used in the present invention is a method for scientific experimentation especially relevant to the fields of biology and chemistry. Through a combination of modern robotics and other specialised laboratory hardware, it allows a researcher to effectively screen large amounts of samples simultaneously.

It is preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helios, Solexa, US Genomics, etcetera, which are herein incorporated by reference.

454 Life Sciences Technology

In certain embodiments, it is preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described allows sequencing of 40 million bases in a single run and is 100 times faster and cheaper than competing technology. The sequencing technology roughly consists of 5 steps: 1) fragmentation of DNA and ligation of specific adaptors to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of /enrichment for beads containing amplified ssDNA molecules on their surface 4) deposition of DNA carrying beads in a PICOTITER™ Plate; and 5) simultaneous sequencing in 100,000 wells by generation of a pyrophosphate light signal. The method will be explained in more detail below.

In a preferred embodiment, the sequencing comprises the steps of:
  (a) annealing adapted fragments to beads, each bead being annealed with a single adapted fragment;
  (b) emulsifying the beads in water-in-oil microreactors, each water-in-oil microreactor comprising a single bead;
  (c) loading the beads in wells, each well comprising a single bead; and generating a pyrophosphate signal.

In the first step (a), sequencing adaptors are ligated to fragments within the combination library. Said sequencing adaptor includes at least a "key" region for annealing to a bead, a sequencing primer region and a PCR primer region. Thus, adapted fragments are obtained.

In a first step, adapted fragments are annealed to beads, each bead annealing with a single adapted fragment. To the pool of adapted fragments, beads are added in excess as to ensure annealing of one single adapted fragment per bead for the majority of the beads (Poisson distribution).

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PICOTITER™ Plate allowing for simultaneous sequencing of a large amount of fragments.

After addition of enzyme-carrying beads, the sequence of the fragments is determined using pyrosequencing. In successive steps, the PICOTITER™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com; www.pyrosequencing.com/section technology. The technology is further applied in e.g. WO 03/004690, WO 03/054142, WO 2004/069849, WO 2004/070005, WO 2004/070007, and WO 2005/003375 (all in the name of 454 Life Sciences), which are herein incorporated by reference. In the present invention, the beads are preferably equipped with primer (binding) sequences or parts thereof that are capable of binding the amplicons, as the case may be. In other embodiments, the primers used in the amplification are equipped with sequences, for instance at their 5'-end, that allow binding of the amplicons to the beads in order to allow subsequent emulsion polymerisation followed by sequencing. Alternatively the amplicons may be ligated with sequencing adaptors prior to ligation to the beads or the surface. The sequenced amplicons will reveal the identity of the identifier and thus of the presence or absence of the restriction fragment in the sample.

Solexa Technologies

One of the methods for high throughput sequencing is available from Solexa, United Kingdom (www.solexa.co.uk) and described inter alia in WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089, WO2005078130. In essence, the method start with adaptor-ligated fragments of genomic DNA. The adaptor-ligated DNA is randomly attached to a dense lawn of primers that are attached to a solid surface, typically in a flow cell. The other end of the adaptor ligated fragment hybridizes to a complementary primer on the surface. The primers are extended in the presence of nucleotides and polymerases in a so-called solid-phase bridge amplification to provide double stranded fragments. This solid phase bridge amplification may be a selective amplification. Denaturation and repetition of the solid-phase bridge amplification results in dense clusters of amplified fragments distributed over the surface. The sequencing is initiated by adding four differently labelled reversible terminator nucleotides, primers and polymerase to the flow cell. After the first round of primer extension, the labels are detected, the identity of the first incorporated bases is recorded and the blocked 3' terminus and the fluorophore are removed from the incorporated base. Then the identity of the second base is determined in the same way and so sequencing continues.

In the present invention, the adaptor ligated restriction fragments or the amplicons are bound to the surface via the primer binding sequence or the primer sequence. The sequence is determined as outlined, including the identifier sequence and (part of) the restriction fragment. Currently available Solexa technology allows for the sequencing of fragments of about 25 base pairs. By economical design of the adaptors and the surface bound primers, the sequencing step reads through the sample identifier, the remains of the recognition sequence of the restriction endonuclease and any optional selective bases. When a 6 bp sample identifier is used, the remains are from the rare cutter EcoRI (AACCT), the use of two selective bases yields an internal sequence of the restriction fragment of 12 bp that can be used to uniquely identify the restriction fragment in the sample.

In a preferred embodiment based on the Solexa sequencing technology above, the amplification of the adapter ligated restriction fragments is performed with a primer that contains at most one selective nucleotide at its 3'end, preferably no selective nucleotides at its 3' end, i.e. the primer is only complementary to the adaptor (a +0 primer).

In alternative embodiments directed to the sequencing methods described herein, the primers used in the amplification may contain specific sections (as alternative to the herein described primer or primer binding sequences) that are used in the subsequent sequencing step to bind the adaptor-capped restriction fragments or amplicons to the surface. These are generally depicted as the key region or the 5'-primer compatible sequence.

Figure 2:
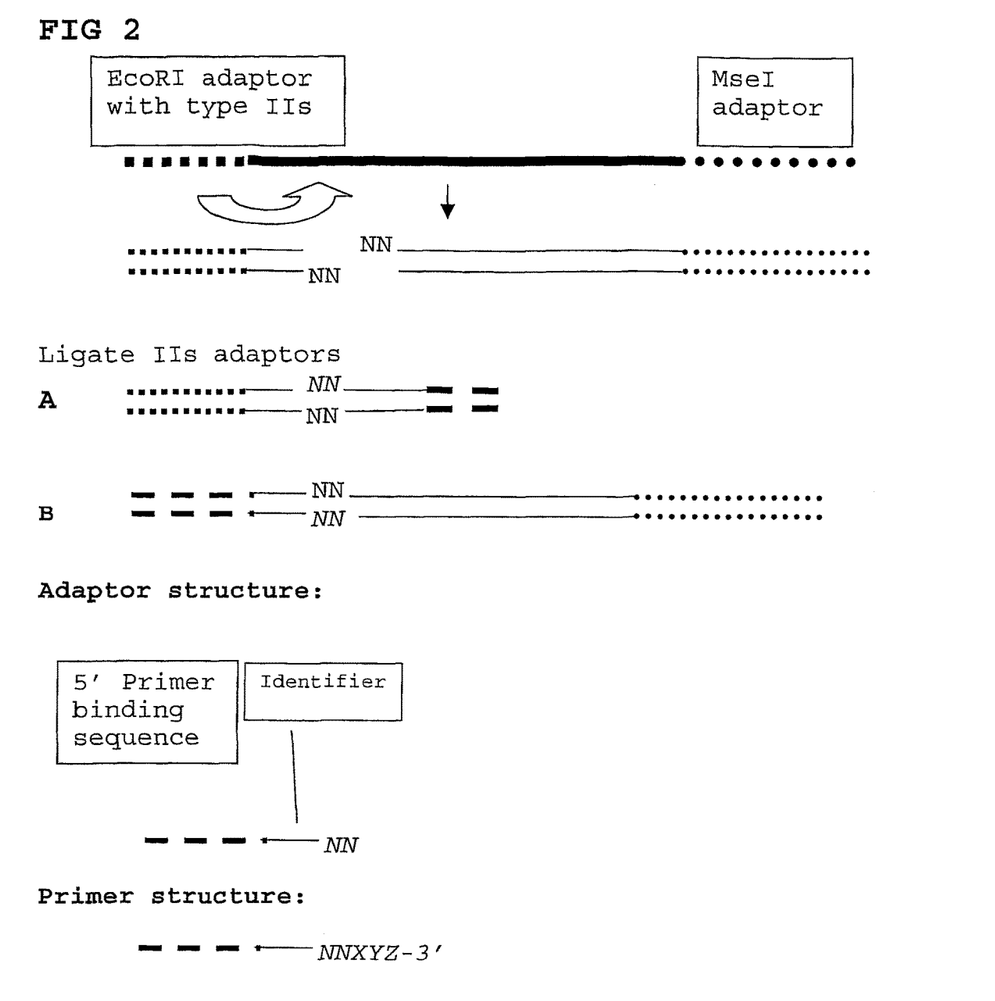
FIG. 2: is a schematic representation of the embodiment wherein a recognition sequence for a type IIs restriction endonuclease is incorporated in the adaptor. After restriction with the type IIs enzyme, type IIs compatible adaptors can be ligated to one or both of the restricted fragments A and B. The type IIs adaptor comprises an optional primer binding (or anchoring) sequence, an identifier and a section containing (degenerate) nucleotides (NN) to hybridize to the overhang of the IIs restriction site. The associated primer may contain one or more selective nucleotides (XYZ) at its 3' end.

In one embodiment of the invention, the nucleic acid sample is digested with at least one restriction enzyme and at least one adapter is ligated that comprises a recognition sequence for a type IIs restriction endonuclease. The subsequent digestion of the adapter-ligated restriction fragment with a type IIs restriction endonuclease yields, as the distance between the recognition and restriction site of a type IIs enzyme is relatively short (up to about 30 nucleotides), a shorter and a longer restriction fragment, to which a IIs restriction site compatible adaptor can be ligated. Typically, the overhang of the IIs-restricted site is unknown such that a set of adaptors may be used that are degenerated in the overhang. After (selective) amplification, the amplicons can be sequenced. The adaptor sequence in this embodiment generally follows: 5'-primer binding site—sample identifier sequence—degenerate type IIs cohesive end sequence-3'. The associated PCR primer generally follows: primer sequence—sample identifier sequence—degenerate type IIs cohesive end sequence—selective nucleotides-3'. The primer used to initiate the sequencing-by-synthesis then generally has the structure: 5'-primer binding site-3'. A size selection step may be preferred after digesting with the IIs enzyme to remove the smaller fragments. As in this embodiment the remains of the restriction site are for this type of enzyme typically in the order of 2-4 bp, this results in combination with a 6 bp sample identifier in the sequencing of 15-17 bp of a restriction fragment.

In a further aspect, the invention relates to kits comprising one or more primer, and/or one or more adaptors for use in the method, aside from conventional components for kits per se. Furthermore the present invention finds application in, amongst others, use of the method for the identification of molecular markers, for genotyping, bulk segregant analysis, genetic mapping, marker-assisted back-crossing, mapping of quantitative trait loci, linkage disequilibrium mapping.

EXAMPLE

DNA was isolated from 2 parents and 88 offspring using conventional methods. Parents (2×) and offspring (=4×) were in duplex with different indices to test reproducibility. Tags used to distinguish samples from each other differed at least in 2 nucleotides from any other tag used in the experiments. Quality is being tested throughout the various steps using agarose and PAA gels.

Example 1

For each DNA sample a restriction-ligation step is performed using EcoRI and MseI as enzymes. Adaptors are based on the hybridizing sequences located on the surface of the Solexa high throughput sequencing system, more in particular the EcoRI adapter contains the P5 sequence (sequence primer part) and the MseI adaptor contains the P7 sequence (bridge PCR primer sequence). The EcoRI adaptor further contains the sample identifying tag. 96 different EcoRI adaptors and one MseI adaptor are used. It is possible to use a degenerated EcoRI adaptor. The template preparation is inclusive of a size selection step by incubation of the mixture for 10 minutes at 80 degrees Celsius after the restriction (EcoRI+MseI) step but prior to the adapter ligation step. Fragments smaller than 130 nt are removed (in a maize sample).

The complexity of the mixture is reduced by a selective preamplification using +1 primers (i.e. containing one randomly selective nucleotide at the 3' end, using 96 EcoRI+1 primers and one MseI+1 primer (or one tag-degenerated EcoRI+1 primer and one MseI+1 primer).

Selective amplification to reduce the complexity of the mixture to the desired size is performed using EcoRI+2 (=P5 side) and MseI+3 (=P7 side) primers necessitating the use of 96 EcoRI+2 primers and one MseI+3 primer. Tail PCR is performed using an EcoRI primer with the P5 bridge PCR primer sequence as the tail. The products are purified using SEPHADEX™ columns. Concentrations are determined and normalised and pools are created. The pools are subjected to massive parallel sequencing based on Solexa technology comprising bridge PCR amplification and sequencing followed by data analysis to determine the genotypes of the parents and the offspring.

An alternative scenario does not use tail PCR, but employs phosphorylated EcoRI+2 primers. Due to the mismatch with the original adaptor, the annealing temperature in the amplification profile is lowered by 3 degrees Celsius to 13 cycles touch-down from 62-53 degrees Celsius followed by 23 cycles at 53 degrees Celsius. After ligation of the adaptor with the P5 bridging PCR sequence, PCR is performed with P5 and P7 bridge PCR primers.

A second alternative scenario is based on standard template preparation as outlined herein before, selective (pre) amplification to reduce the complexity. Selective amplification is performed with primers that contain the reconstituted EcoRI and MseI restriction sites. This allows for removal of the adaptor sequences prior to sequencing, thereby reducing the amount of data to be analysed. Purification of the products by SEPHADEX™ columns to remove remains of Taq DNA polymerase. Template preparation wherein (reconstituted site) adapter sequences are replaced by Solexa adaptors using ten-fold increased EcoRI adaptor and EcoRI enzyme to compensate for the increased number of EcoRI sites compared to genomic DNA. The Solexa EcoRI adaptors also contain the tags, hence 96 tagged Solexa EcoRI adaptors are needed. The bottom strand of the adaptor is blocked at the 3' end (in this case by 3' amino) to block extension by a polymerase. PCR is performed with P5 and P7 bridge PCR primers. Products are purified by Qiagen columns.

Example 2

Sequence-based detection of AFLP fragments was performed using Solexa's Clonal Single Molecule Array (CSMA™) technology, a Sequencing-by-Synthesis platform capable of analyzing up to 40 million individual fragments in a single sequence run.

The experimental sequence involves AFLP template preparation, selective (AFLP) amplification, single molecule bridge amplification and sequencing of millions of sequence tags from one restriction enzyme end of the AFLP fragments. Maize parental lines B73 and Mo17 and 87 Recombinant Inbred Lines (RILs) were used and sequenced over 8.9 million EcoRI AFLP fragment termini were sequenced to provide proof-of-principle for sequence-based AFLP detection.

Parental lines B73 and Mo17 and 87 RILs were selected. AFLP templates were prepared using restriction enzyme combination EcoRI/MseI. Selective amplification was performed using+2/+3 AFLP primers.

Template fragments for Solexa CSMA bridge amplification were prepared by performing a second restriction/ligation using EcoRI adaptors containing unique 5 bp sample identification (ID) tag sequences. Parental lines and three RIL samples were included twice using different 5 bp sample ID tags to measure within-experiment reproducibility.

Sequence-based AFLP markers were identified by extracting 27 bp sequence tags observed at different frequencies in B73 and Mo17, segregating in the RIL offspring.

AFLP Marker Distribution AFLP+3/+3: Sequence/Gel-Based

|  | total | EcoRI + 3 base | | | |
|---|---|---|---|---|---|
|  |  | +A | +C | +G | +T |
| # sequence tag AFLP markers | 125 | 34 | 37 | 37 | 17 |
| # gel-based AFLP markers | 82 | 29 | 18 | 17 | 18 |

Reproducibility Sequence Tag AFLP Marker Duplos 3 RIL Offspring

| | |
|---|---|
| # sequence tag AFLP markers scored | 125 |
| # number of data-points in comparison | 375 |
| # data-points identical for duplos | 372 |
| % concordancy within experiment duplos | 99.2% |

Conventional Slab Gel Detection:

| AFLP marker | B73 | Mo17 | 1 | 2 | 3 | 4 | 5 | 6 | 7 | 8 | 9 | 10 | 11 | 12 |
|---|---|---|---|---|---|---|---|---|---|---|---|---|---|---|
| E36/M50-175.9 | − | + | + | − | − | − | − | + | − | + | − | − | − | + |
| E36/M50-280 | + | − | + | − | − | + | − | + | − | + | − | + | − | − |
| E36/M50-405.8 | − | + | + | − | − | + | + | + | + | + | − | + | − | + |
| E36/M50-243.7 | + | − | + | − | − | − | − | + | + | + | + | + | + | + |
| E36/M50-124.02 | + | − | + | − | + | + | + | + | − | − | − | − | + | + |
| E36/M50-379 | + | − | + | − | − | + | + | + | + | + | + | + | − | + |
| E36/M50-468.9 | + | − | + | − | + | + | − | + | − | + | + | + | + | + |

Sequence-based AFLP marker data were compared to AFLP marker scores obtained by conventional AFLP fingerprinting using length-based detection of the four corresponding EcoRI/MseI +3/+3 primer combinations.

Sequence Run Statistics 5 Flow Cells

| | |
|---|---|
| # sequence tags generated | 8,941,407 |
| # sequence tags with known sample IDs | 8,029,595 |
| # different sequence tags with known sample IDs | 206,758 |
| # Mbp sequence data generated | 241.4 |
| frequency range total # sequence tags per sample | 55,374-112,527 |
| # sequence tag AFLP markers | 125 |
| frequency range sequence tag AFLP markers in parent scoring present | 90-17,218 |

Sequence Tag AFLP Marker Definition and Scoring tabulate sequence tags representation per sample remove sequence tags with unknown sample IDs normalize sample representation based on total sequence tags per sample remove sequence tags with >2 fold frequency difference in parental duplos average tag frequencies parental duplos define sequence tag AFLP marker if frequency P1/P2 exceeds threshold value score presence/absence of sequence tag markers in RIL offspring Solexa-Based Detection

| AFLP marker | B73 | Mo17 | 1 | 2 | 3 | 4 | 5 | 6 | 7 | 8 | 9 | 10 | 11 | 12 |
|---|---|---|---|---|---|---|---|---|---|---|---|---|---|---|
| CGGCGACGTACCGC | − | + | + | − | − | − | − | + | − | + | + | − | − | + |
| CTAGTAATTATTCC | + | − | + | − | + | − | + | + | + | − | + | − | − | − |
| CAGCGCCTTCTCCT | − | + | + | − | − | − | + | + | + | + | − | + | − | + |
| CAGAACTCTGACTT | + | − | + | − | − | − | − | − | + | + | + | + | + | + |
| CAAATCTGTTAGAT | + | − | + | − | + | + | + | + | − | + | − | − | + | + |
| CATGAAGGATTTAT | + | − | + | − | − | + | + | + | + | + | + | + | − | + |
| CAAACAGACAACCG | + | − | + | − | + | + | − | + | − | + | + | + | + | + |

The viability sequenced-based AFLP marker detection was generated using Solexa's CSMA technology. whereby a larger number of AFLP markers is scored using sequence-based detection than on conventional slab gels, presumably due to improved resolution (fragment size) and deep sequencing which also captures low abundance fragments. Marker data vector comparisons reveal similar segregation patterns between sequence-based detection and slab gel detection: proof of concordancy awaits sequencing gel-based AFLP markers.

The invention claimed is:

1. A method for detecting one or more polymorphisms in a plurality of nucleic acid samples, comprising:

obtaining a pool of amplicons from the plurality of nucleic acid samples, which comprises amplifying the nucleic acid samples or fragments thereof using one or more primers, wherein the amplicons derived from each of the nucleic acid samples are tagged with a unique sample-specific identifier sequence;

sequencing the pool of amplicons to obtain sequence reads, wherein the sample-specific identifier sequence and at least part of the sequence of the nucleic acid samples are sequenced by high-throughput sequencing; and detecting one or more polymorphisms in the plurality of nucleic acid samples by comparing the sequence reads and using the identifier sequence to assign the polymorphisms to the nucleic acid samples.

2. The method according to claim 1, wherein the one or more polymorphisms comprise single nucleotide polymorphism (SNP).

3. The method according to claim 1, wherein the high-throughput sequencing is performed on a solid support and comprises annealing the amplicons to the solid support and amplifying the annealed amplicons.

4. The method according to claim 1, wherein the high-throughput sequencing is based on Sequencing-by-Synthesis.

5. The method according to claim 1, wherein the high-throughput sequencing comprises the steps of: annealing the amplicons to beads, each bead annealing with a single amplicon; emulsifying the beads in water-in-oil micro reactors, each water-in-oil micro reactor comprising a single bead; performing emulsion PCR to amplify the amplicons on the surface of beads; optionally, selecting/enriching beads containing amplified amplicons; loading the beads in wells, each well comprising a single bead; and determining the nucleotide sequence of the amplified amplicons using generating a pyrophosphate signal.

6. The method according to claim 1, wherein the high-throughput sequencing comprises the steps of: annealing the amplicons to a surface containing first and second primers or first and second primer binding sequences respectively, performing bridge amplification to provide clusters of amplified amplicons, determining the nucleotide sequence of the amplified amplicons using labeled reversible terminator nucleotides.

7. The method according to claim 1, wherein the amplicons are obtained by amplifying the nucleic acid samples or fragments thereof using at least one primer comprising at its 3' end one or more nucleotides hybridizable to the nucleic acid samples.

8. The method according to claim 1, wherein the sample-specific identifier sequence is 4-16 bp.

9. The method according to claim 1, wherein the sample-specific identifier sequence is 4-10 bp.

10. The method according to claim 1, wherein the sample-specific identifier sequence is 4-6 bp.

11. The method according to claim 1, wherein the sequencing is performed at least 6 times.

12. The method according to claim 1, wherein the sequencing is performed at least 9 times.

* * * * *